(12) United States Patent
Wang et al.

(10) Patent No.: US 12,379,299 B2
(45) Date of Patent: Aug. 5, 2025

(54) METHODS AND SYSTEMS FOR A PARALLEL FLOW CORE SAMPLE HOLDER

(71) Applicant: SAUDI ARABIAN OIL COMPANY, Dhahran (SA)

(72) Inventors: Jinxun Wang, Dhahran (SA); Abdulkareem M. Al-Sofi, Dhahran (SA); Ming Han, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 301 days.

(21) Appl. No.: 18/066,020

(22) Filed: Dec. 14, 2022

(65) Prior Publication Data
US 2024/0201064 A1 Jun. 20, 2024

(51) Int. Cl.
*G01N 15/08* (2006.01)
*G01N 33/24* (2006.01)

(52) U.S. Cl.
CPC .......... *G01N 15/082* (2013.01); *G01N 33/24* (2013.01)

(58) Field of Classification Search
CPC ... G01N 15/08; G01N 15/0806; G01N 15/082
See application file for complete search history.

(56) References Cited

U.S. PATENT DOCUMENTS

| | | | | |
|---|---|---|---|---|
| 4,710,948 A | * | 12/1987 | Withjack | G01N 23/04 378/208 |
| 5,161,407 A | * | 11/1992 | Ankeny | G01N 15/0893 73/38 |
| 10,094,814 B2 | * | 10/2018 | Wang | G01N 33/24 |
| 2016/0109334 A1 | | 4/2016 | Collins et al. | |
| 2018/0045704 A1 | | 2/2018 | Al-Otaibi et al. | |
| 2021/0116352 A1 | | 4/2021 | Yue et al. | |

FOREIGN PATENT DOCUMENTS

| | | |
|---|---|---|
| CN | 205941296 U | 2/2017 |
| CN | 209231172 U | 8/2019 |
| CN | 212432911 U | 1/2021 |
| CN | 113607622 A | 11/2021 |

OTHER PUBLICATIONS

Liu et al., Parallel Double-tube Oi-displacing Rock Core Holder (CN 212432911 U), Jan. 2021, FIT Machine Translation (Year: 2021).*

* cited by examiner

*Primary Examiner* — Erika J. Villaluna
(74) *Attorney, Agent, or Firm* — Osha Bergman Watanabe & Burton LLP

(57) ABSTRACT

A core sample holder for testing core samples from a well includes a body having a wall defining a cavity. At least two sleeves are disposed within the cavity parallel to each other. Each sleeve of the at least two sleeves is configured to individually hold the core samples. At least one cap is removably coupled to an inner surface of the wall. A tube extends from each end of the at least two sleeves to be a dedicated inlet at a first end of each sleeve and a dedicated outlet at a second end of each sleeve.

20 Claims, 9 Drawing Sheets

METHODS AND SYSTEMS FOR A PARALLEL FLOW CORE SAMPLE HOLDER

BACKGROUND

In the oil and gas industry, coring operations may be performed to remove rock samples from a well. Typically, a core bit may be used to drill out core samples of the well. The core samples may be taken at various depths within the well. Additionally, the core samples may be of various shapes and sizes. For example, the core sample may be in a shape of a cylinder having various dimensions. The core samples are then brought to the surface for analysis. Analysis of the core samples may provide valuable data to assess a productivity of the well to produce hydrocarbons. For example, formation properties of the well may be determined such as porosity, permeability, fluid saturation, grain density and other characteristics to provide insight on the downhole conditions.

Typically, to analyze a core sample, the core sample may be placed in core testing devices or apparatus to run various tests. Conventional core testing devices comprise an assembly of rigid piping components to test a single core sample. For example, a conventional core testing device may include metal pipe to hold the single core sample. However, to analyze the core sample with many varied injection fluids or different injection strategies, conventional methods require separate test for each of the injection fluids or injection strategies on the single core sample. Additionally, to analyze multiple core samples, conventional methods require the core samples being loaded in different core testing devices.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, the embodiments disclosed herein relate to a core sample holder for testing core samples from a well. The core sample holder may include a body having a wall defining a cavity; at least two sleeves disposed within the cavity parallel to each other, each sleeve of the at least two sleeves is configured to individually hold the core samples; at least one cap removably coupled to an inner surface of the wall; and a tube extending from each end of the at least two sleeves to be a dedicated inlet at a first end of each sleeve and a dedicated outlet at a second end of each sleeve.

In another aspect, the embodiments disclosed herein relate to a core testing system for testing core samples from a well. The core testing system may include a core sample holder having a body to hold at least two core and sleeve assemblies parallel to each other within a cavity of the body. Each of the at least two core and sleeve assemblies may include a sleeve; a core sample inserted in the sleeve; a first plug closing a first end of the sleeve and a second plug closing a second end of the sleeve to isolate the core sample; and a pair of tubes fluidly coupled to a tubing fitting in the first plug and the second plug to form a dedicate inlet at the first plug and a dedicate outlet at the second plug. The core testing system may also include at least one pump fluidly coupled to the dedicate inlet extending out of the body of the core sample holder. The at least one pump may be configured to inject fluids into each of the at least two core and sleeve assemblies.

In yet another aspect, the embodiments disclosed herein relate to a method for testing core sample from a well. The method may include collecting at least two core samples; placing each core sample of the at least two core samples individually within a corresponding sleeve to form at least two core and sleeve assemblies in parallel; disposing the at least two core and sleeve assemblies within a cavity of a core sample holder; applying a target confining pressure to the at least two core samples; and injecting fluids through the at least two core samples.

Other aspects and advantages will be apparent from the following description and the appended claims.

BRIEF DESCRIPTION OF DRAWINGS

The following is a description of the figures in the accompanying drawings. In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, shapes of the elements as drawn are not necessarily intended to convey any information regarding the actual shape of the elements and have been solely selected for ease of recognition in the drawing.

DETAILED DESCRIPTION

Figure 1:
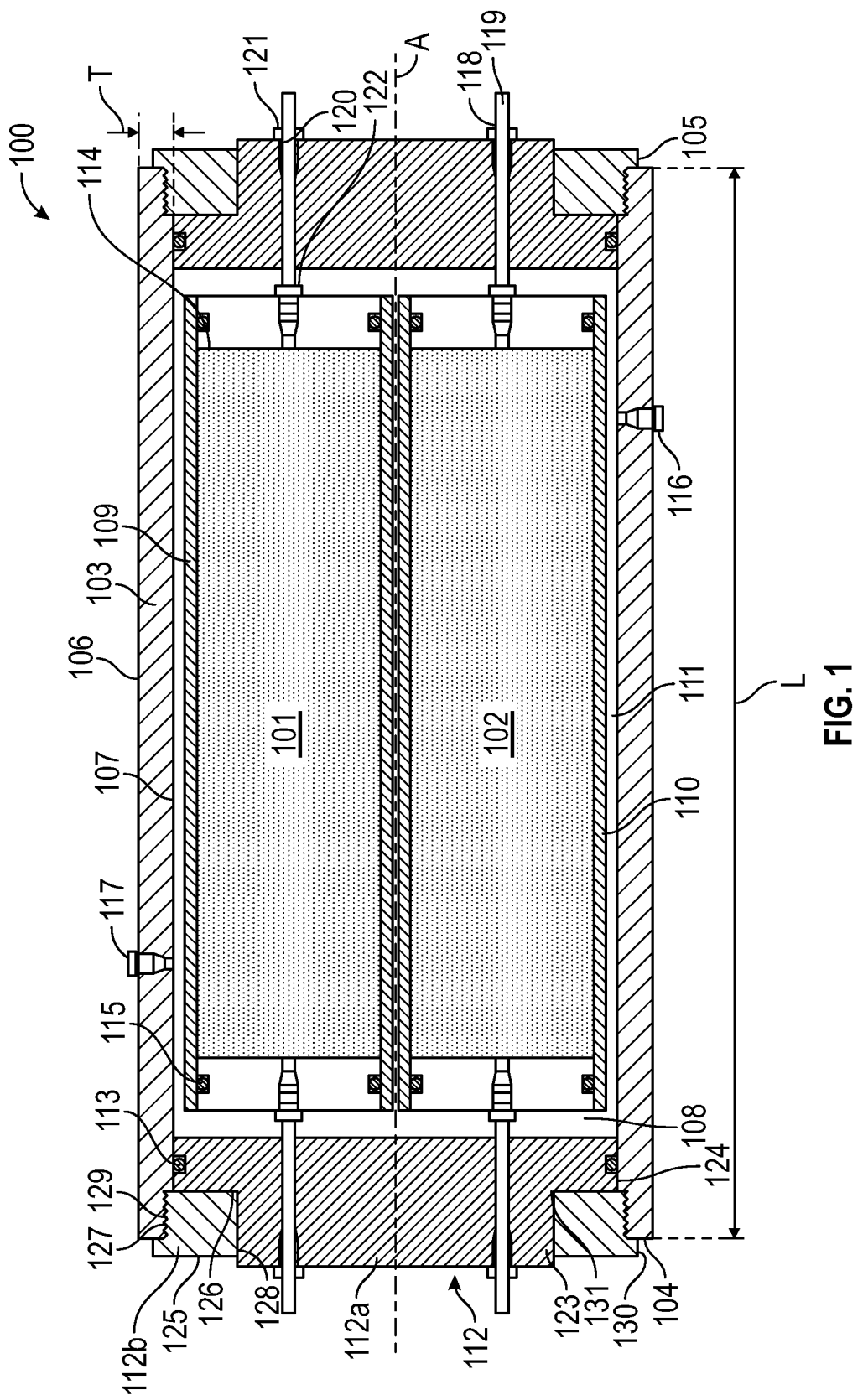
FIG. 1 illustrates a cross-sectional side view of a core sample holder in accordance with one or more embodiments of the present disclosure.

Embodiments of the present disclosure will now be described in detail with reference to the accompanying Figures. Like elements in the various figures may be denoted by like reference numerals for consistency. Further, in the following detailed description of embodiments of the present disclosure, numerous specific details are set forth in order to provide a more thorough understanding of the claimed subject matter. However, it will be apparent to one of ordinary skill in the art that the embodiments disclosed herein may be practiced without these specific details. In other instances, well-known features have not been described in detail to avoid unnecessarily complicating the description. Additionally, it will be apparent to one of ordinary skill in the art that the scale of the elements presented in the accompanying Figures may vary without departing from the scope of the present disclosure.

As used herein, the term "coupled" or "coupled to" or "connected" or "connected to" "attached" or "attached to" may indicate establishing either a direct or indirect connection and is not limited to either unless expressly referenced as such. Wherever possible, like or identical reference numerals are used in the figures to identify common or the same elements. The figures are not necessarily to scale and certain features and certain views of the figures may be shown exaggerated in scale for purposes of clarification. In addition, any terms designating tubular (i.e., any tubular extending from a first end to a second end with a conduit between the ends) should not be deemed to limit the scope of the disclosure. As used herein, fluids may refer to slurries, liquids, gases, and/or mixtures thereof. Additionally, as used herein, core samples may refer to cylindrical shaped rocks drilled from a formation of a well. While it is noted that the core samples are cylindrical shaped rocks, the core samples may be any size or shape without departing from the scope of the present disclosure. The embodiments are described merely as examples of useful applications, which are not limited to any specific details of the embodiments herein.

Embodiments disclosed herein relate to flooding experiments in, for example, the oil and gas industry, to obtain fluid and flow properties from a plurality of core samples in parallel or at the same time. More specifically, embodiments disclosed herein relate to loading a plurality of core samples into a core sample holder to conduct flooding experiments. With the plurality of core samples within the core sample holder, a single injection fluid or a variety of injection fluids may be injected to each core sample to conduct a plurality of flooding experiments at a same time. It is further envisioned that the same injection fluid may also be injected simultaneously to all core samples to simulate parallel flow.

It is to be further understood that the various embodiments described herein may be used in various stages of core testing to analyze and measure core sample properties, such as simulating flooding experiments in the oil & gas industry to obtain fluid permeability and flow properties, chemical analysis, hydrocarbon saturation, grain density, enhanced oil recovery (EOR), formation damage evaluations, etc., and in other industries, such as construction and the study of geology. Flooding experiments may refer to core flooding testing that may mimic reservoir conditions (i.e., pressure and temperature) on a core sample. For example, a pressure or flow of fluid may be applied across or through the core sample that corresponds to a similar pressure or flow experienced by rock in a reservoir. Initially, the core sample may be disposed in a simulated formation brine, oil, or combination of brine and oil at the start of the core flooding test. Fluids, such as crude oil, simulated reservoir brine, drilling muds, acids, and/or other chemicals, may then be injected into the core sample holder while various measurements of the core and fluid are recorded. Core flooding tests recorded measurements and results may then be used to guide mathematical models and extract critical simulation parameters for well operations.

In conventional methods, core flooding tests are conducted to simulate fluid flow through a certain uniform reservoir region, and only one core sample, either a single plug or a composite sample, is used in each test. Such conventional methods are time consuming, and some core analysis require a plurality of core flooding tests. For example, in some embodiments, core analysis may need a variety of injection fluids or different injection strategies for evaluation and conventional methods can only test one core sample at a time. Therefore, it is advantageous to conduct a plurality of core flooding tests simultaneously using a same core flooding setup. In many reservoirs, heterogeneity is commonly observed, for examples, layered reservoirs with widely varied permeabilities. Thus, it is also advantageous to conduct the core flooding tests to simulate the parallel flow through a few varied types of rock samples.

The different embodiments described herein may provide a core sample holder to conduct various tests on a plurality of core samples in parallel or at the same time. The core sample holder may include a body having a cavity defined therein and at least two sleeves disposed within the cavity to each hold a core sample. For example, a plurality of core samples may be individually loaded into a corresponding sleeve of the at least two sleeves, and each core and sleeve assembly are disposed into the cavity of the core sample holder. Additionally, the core and sleeve assemblies may be axially parallel to each other. In some embodiments, a hydraulic pressure may be applied to confine the plurality of core samples within the core sample holder. With the plurality of core samples within the core sample holder, a single injection fluid or a variety of injection fluids may be injected to each core and sleeve assembly to conduct a plurality of flooding experiments at a same time. It is further envisioned that the same injection fluid may also be injected simultaneously to all core and sleeve assemblies to simulate parallel flow. Accordingly, the core sample holder disclosed herein improves flooding experiment efficiency and facilitates studies of a flow of fluids through the plurality of core samples (i.e., reservoir rocks). In addition, the core sample holder may simulate all types of production processes at a well, such as fluid flow in a multi-layer reservoir without or with partial crossflow, waterflooding, and chemical flooding for improved or enhanced oil recovery. Overall, the core sample holder as described herein may reduce product engineering, reduction of assembly time, hardware cost reduction, and weight and envelope reduction.

Turning to FIG. 1, a cross-sectional view of a core sample holder 100 to hold a plurality of core samples (101, 102) in accordance with one or more embodiments of the present disclosure is shown. In one or more embodiments, the core sample holder 100 may be coupled to testing equipment, as described in FIGS. 2-6, to conduct core sampling analysis. For example, fluids may be injected into the core sample holder 100 and increase or decrease a pressure within the core sample holder 100 to simulate flooding of a reservoir as well as downhole conditions on the core samples within the core sample holder 100. Additionally, the testing equipment may include or be connected to a computer system (as described in FIG. 10) to store, calculate and display results from various tests using the core sample holder 100.

The core sample holder 100 may have a body 103 extending a length L from a first end surface 104 to a second end surface 105. One skilled in the art will appreciate that the length L of the body 103 may be any length selected based on a length of the plurality of core samples (101, 102). In other words, the length L of the plurality of core samples (101, 102) may be selected to ensure various lengths of the plurality of core samples (101, 102) may be positioned within the core sample holder 100. For example, the length L of the body 103 may have a value to hold varied ranges of core lengths from 1.0 inch to 6 inches or from 6 inches to 12 inches. While it is noted that two core samples 101, 102 are shown within the body 103, the core sample holder 100 may hold any number of core samples equal to or greater than two core samples without departing form the scope of the present disclosure. In one or more embodiments, the body 103 may be in the shape of a hollow cylinder. However, in some embodiments, the body 103 may be a hollow rectangular prism, or a hollow cube, or any other shaped housing having a cavity defined therein, such that the plurality of core samples (101, 102) may be positioned within the core sample holder 100. Additionally, the plurality of core samples (101, 102) may be parallel to each other and offset to an axis A of the body 103.

In one or more embodiments, the body 103 may have a wall with a thickness T measured from an outer surface 106 of the wall to an inner surface 107 of the wall. It is further envisioned that the wall of the body 103 may made be made from a reinforced material, such as plastic, stainless steel (316L), Hastelloy, Monel, titanium, Inconel, or other materials, to hold the plurality of core samples (101, 102). In a non-limiting example, the thickness T of the body 103 may have a value to allow for various pressures without damaging the wall made from the reinforced material. In other words, the thickness T of the body 103 is selected to ensure structural integrity of the core sample holder 100 based on testing pressures and temperatures.

In some embodiments, the inner surface 107 may define a cavity 108 within the wall and the cavity 108 may have openings at the first end surface 104 and the second end surface 105 opposite each other. The cavity 108 allows for the plurality of core samples (101, 102) to be inserted within the core sample holder 100. For example, the body 103 may have an inner diameter sized such that the cavity 108 may accommodate all different sizes of core sample sizes.

In one or more embodiments, the plurality of core samples (101, 102) may be individually inserted into corresponding sleeves (109, 110) which are then disposed in the cavity 108. Additionally, the sleeves (109, 110) extend in the same axial direction as the axis. It is further envisioned that the sleeves (109, 110) may be a tube made from a rubber or heat-shrinkable material molded to a size and shape of the plurality of core samples (101, 102). For example, an elastic rubber such as Viton, Kalrez, or Aflas may be used to provide a radial compressive force exerted on the plurality of core samples (101, 102) through the sleeves (109, 110) via fluids outside the sleeves (109, 110). It is further envisioned that lead may be used in place of the rubber or heat-shrinkable material. In some embodiments, the sleeves (109, 110) may have an inner diameter ranging from 1.0 inch to 1.5 inches. In some embodiments, the sleeves (109, 110) may be sized smaller than 1.0 inch to 1.5 inches to accommodate smaller core samples. Additionally, the sleeves (109, 110) may be sized larger than 1.0 inch to 1.5 inches to accommodate larger core samples.

After the plurality of core samples (101, 102) are inserted in the corresponding sleeves (109, 110), plugs 114 may be inserted at both ends of the corresponding sleeves (109, 110). The plugs 114 may secure and hold the plurality of core samples (101, 102) within the corresponding sleeves (109, 110). The plugs 114 may aid in pressurizing the plurality of core samples (101, 102) by sealing pressure within the corresponding sleeves (109, 110). Furthermore, a sealing element 115, such as an O-ring or elastomer seal, may be provided to seal any gap between the plugs 114 and the sleeves (109, 110).

Still referring to FIG. 1, in a non-limiting example, the sleeves (109, 110) may be spaced from the inner surface 107 of the body 103 such that void space 111 is formed between the sleeves (109, 110) and the body 103. It is further envisioned that the sleeves (109, 110) may also be spaced apart from each other. In some embodiments, the sleeves (109, 110) may be against each other and/or tied together in a bundle. While it is noted that two sleeves (109, 110) are shown, the core sample holder 100 may include any number of sleeves equal to or greater than two sleeves without departing from the scope of the present disclosure. Additionally, the sleeves (109, 110) may have a length extending axially within the body 103. For example, the length of the sleeves (109, 110) may be shorter than length L of the body 103. Further, in some embodiments, the sleeves (109, 110) may be angled from the axis A of the body 103 such that the sleeves (109, 110) may be slanted or angled within the cavity 108.

In one or more embodiments, caps 112 may be provided in the openings of the body 103 at the first end surface 104 and the second end surface 105 to isolate and seal the plurality of core samples (101, 102) within the core sample holder 100. For example, the caps 112 may include threads to removably couple to threads on the inner surface 107 adjacent to the first end surface 104 and the second end surface 105. It is further envisioned that the caps 112 may be a flexible or adjustable type end caps to accommodate different lengths of the plurality of core samples (101, 102). For example, a distance between the flexible or adjustable type end caps and the plurality of core samples (101, 102) adjustable. In some embodiments, one or both caps 112 may be a fixed type end cap such that a distance between the fixed type end cap and the plurality of core samples (101, 102) is fixed. Additionally, a sealing element 113, such as an O-ring or elastomer seal, may be provided to seal any gap between the caps 112 and the inner surface 107.

In some embodiments, each cap includes a cap body 112a and a cap retainer nut 112b as two separate components. It is further envisioned that the cap body 112a and the cap retainer nut 112b may be molded or welded together to form one uniform cap. Additionally, a snap ring may be used to hold the cap retainer nut 112b and the cap body 112a together. The cap body 112a is inserted into the openings of the body 103 such that the cap body 112a is within the cavity 108 of the body 103. In some embodiments, at a first end, a flange 123 of the cap body 112a extends upward from a load shoulder 131. The flange 123 may extend out the body 103 past the corresponding end surface (104, 105). Additionally, at a second end extending axially from the first end, the cap body 112a may have a sealing surface 124 to seal against the inner surface 107 of the body 103. On the sealing surface 124, the cap body 112a is provided with the sealing element 113.

In one or more embodiments, the cap retainer nut 112b may be a ring extending axially from a first end surface 125 to a second end surface 126. An exterior surface 127 is formed from the first end surface 125 to the second end surface 126 as the outer surface of the cap retainer nut 112b. In addition, an interior surface 128 is formed from the first end surface 111 to the second end surface 112 as the inner surface of the bonnet retainer nut 102 such that a passage is formed. It is noted that passage may have a diameter equal to or greater than a diameter of the flange 126 of the cap body 112a but less than a diameter of the second end of the cap body 112a. Additionally, the second end surface 126 contacts the load shoulder 131 of the cap body 112a to prevent the cap body 112a from moving out of the body 103. Threads may be provided on the exterior surface 127 of the cap retainer nut 112b to form a connection surface of the cap. Further, threads 129 may be provided on the inner surface 107 of the body 103 to form a connection surface that is to be connected to the connection surface (i.e., threads) of the cap retainer nut 112b. For example, the threads 129 may be provided on a portion (e.g., a surface or cavity) of the inner surface 107 adjacent to the end surfaces (104, 105) to form the connection surface to engage the threads of the cap retainer nut 112b and lock/retain the cap body 112a within the body 103. The cap retainer nut 112b allows the cap body 112a to move in an axial direction while preventing rotation movement. While it is noted that FIG. 1 shows threads (127, 129) to make-up the cap retainer nut 112*b*. to the body 103, one of skill in the art would understand that the use of threads is merely a non-limiting example, and any different type of mechanical coupler may be used without departing from the present scope of the disclosure to couple the cap retainer nut 112*b* to the valve block body 103. It is further envisioned that the cap retainer nut 112*b* may include a shoulder 130 to land on the corresponding end surface (104, 105).

With the caps 112 removably coupled to the body 103, a fluid, such as hydraulic oil or water or a gas, may be pumped into and fill the void space 111. For example, the body 103 may be provided with a first port 116, extending through the wall, to allow fluids to enter the cavity and fill the void space 111. The first port 116 may be provided on a bottom of the body 103. Additionally, the body 103 may be provided with a second port 117, extending through the wall, to release air being pushed out as the void space 111 is being filled with the fluid. The second port 117 may be provided on a top of the body 103. Once the void space 111 is filled with the fluid, the second port 117 is closed to apply a target confining pressure to the plurality of core samples (101, 102).

As shown in FIG. 1, in one or more embodiments, a plurality of tubes 119 provide an inlet at one the first end surface 104 or the second end surface 105 and an outlet at one the first end surface 104 or the second end surface 105 for the core sample holder 100. It is noted that either end surface (104, 105) can be provided as an inlet or outlet. In some embodiments, the inlet and outlet may be alternatively switched during testing. The number of tubes 119 may correspond to number of core samples (101, 102) in the core sample holder 100 such that each core sample has a dedicated inlet and a dedicated outlet. The plurality of tubes 119 may be flow lines to allow fluids to flow therein and to the plurality of core samples (101, 102). For example, the plurality of tubes 119 are inserted into tubing fittings 122 in the plugs 114 and extend out of through holes 118 of the cap 112 for attachment to a fluid source. The tubing fitting 122 may be ferrules and glands or nuts type fitting. Additionally, the tubing fitting 122 may be coaxial with an axis of the corresponding sleeve (109, 110) to allow for an even distribution of fluids flowing into the plurality of core samples (101, 102). It is further envisioned that the plurality of tubes 119 may slightly move axially in the caps 112 such that a sample confining pressure is applied onto the plurality of core samples (101, 102) in both radial and axial directions.

In one or more embodiments, the caps 112 are provide with the through holes 118 for the plurality of tubes 119 to extend through and out of the body 103. For example, the through holes 118 extend from the first end of the cap body 112*a* to the second end of the cap body 112*a*. The number of through holes 118 may correspond to the number of tubes 119 for each core sample. A diameter of each through holes 118 may be larger than an outer diameter of the tubes 119 so that the tubes 119 thereby forming a gap so that the tubes 119 may flex within the through holes 118. To seal this gap, an O-ring 120 or elastomer seal may be inserted between the through holes 118 and the plurality of tubes 119. Further, a nut 121, such as a gland nut, may be used to compress the O-ring 120 within the caps 112.

Figure 2:
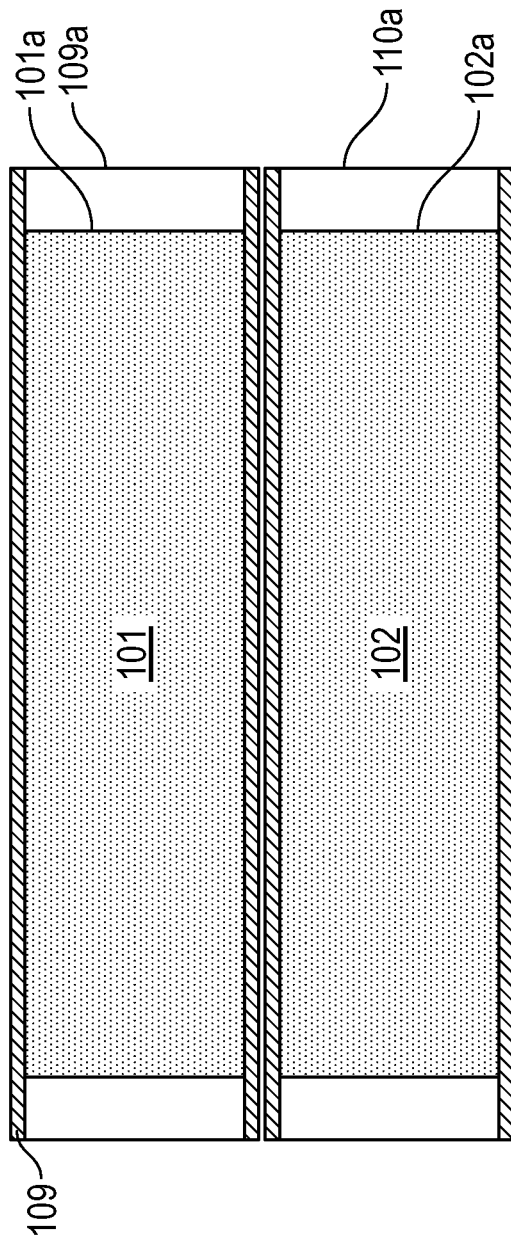
FIGS. 2-6 illustrate a cross-sectional side view of the core sample holder of FIG. 1 in a core testing set up in accordance with one or more embodiments of the present disclosure.

Now referring to FIGS. 2-6, an example of a core testing setup using the core sample holder 100 of FIG. 1 is illustrated. First, as shown in FIG. 2, a first core sample 101 is loading into a first sleeve 109 and a second core sample 101 is loading into a second sleeve 110. Additionally, a length of each core sample 101, 102 is less than a length of the corresponding sleeve 109, 110 such that there is space between an end face 101*a*, 102*a* of each core sample 101, 102 and end faces 109*a*, 110*a* of the corresponding sleeves 109, 110.

In one or more embodiments, the first sleeve 109 and the second sleeve 110 may be a tube made from a rubber material molded to a size and shape of the first core sample 101 and the second core sample 102, respectively. The rubber material may aid in creating a friction fit in the first sleeve 109 and the second sleeve 110 with the first core sample 101 and the second core sample 102, respectively. Alternatively, if the first sleeve 109 and the second sleeve 110 are made from a heat-shrinkable material, the first sleeve 109 and the second sleeve 110 are heated to shrink and form around the first core sample 101 and the second core sample 102, respectively.

Figure 3:
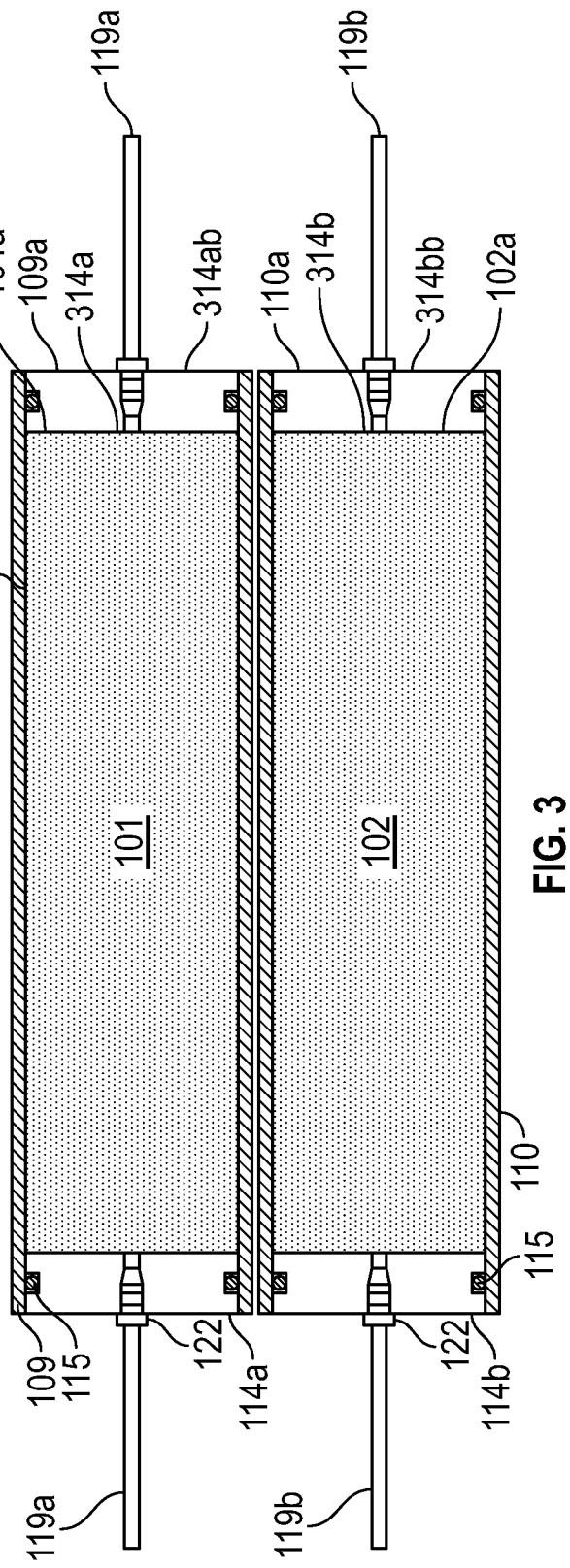

As shown in FIG. 3, with the first core sample 101 and the second core sample 102 loaded into the first sleeve 109 and the second sleeve 110, respectively, plugs (114*a*, 114*b*) are inserted at both ends of each sleeve 109, 110. For example, a first pair of plugs 114*a* is inserted at the ends of the first sleeve 109 to form a first core and sleeve assembly. A first plug end face 314*a* of each plug 114*a* contacts each end face 101*a* of the first core sample 101. A second plug end face 314*ab* of each plug 114*a* is flush with the end faces 109*a* of the first sleeve 109. In some embodiments, the second plug end face 314*ab* may be spaced from the end faces 109*a* such that each plug 114*a* is inserted further inside the first sleeve 109. Additionally, a second pair of plugs 114*b* is inserted at the ends of the second sleeve 110 to form a second core and sleeve assembly. A first plug end face 314*b* of each plug 114*b* contacts each end face 102*a* of the second core sample 102. A second plug end face 314*bb* of each plug 114*b* is flush with the end faces 110*a* of the second sleeve 110. In some embodiments, the second plug end face 314*bb* may be spaced from the end faces 110*a* such that each plug 114*b* is inserted further inside the second sleeve 110. It is further envisioned that each of the plugs 114*a*, 114*b* is provided with the sealing element 115, such as an O-ring or elastomer seal, to seal any gap between each plug 114*a*, 114*b* and corresponding sleeves 109, 110.

In one or more embodiments, a first pair of tubes 119*a* is fluidly coupled to the first core sample 101. For example, each plug 114*a* is provided with the tubing fitting 122 extending from the second plug end face 314*ab* to the first plug end face 314*a*. The first pair of tubes 119*a* are coupled to the tubing fitting 122 to allow fluid communication with the first core sample 101. Additionally, a second pair of tubes 119*b* is fluidly coupled to the second core sample 102. For example, each plug 114*b* is provided with the tubing fitting 122 extending from the second plug end face 314*bb* to the first plug end face 314*b*. The second pair of tubes 119*b* are coupled to the tubing fitting 122 to allow fluid communication with the second core sample 102.

Figure 4:
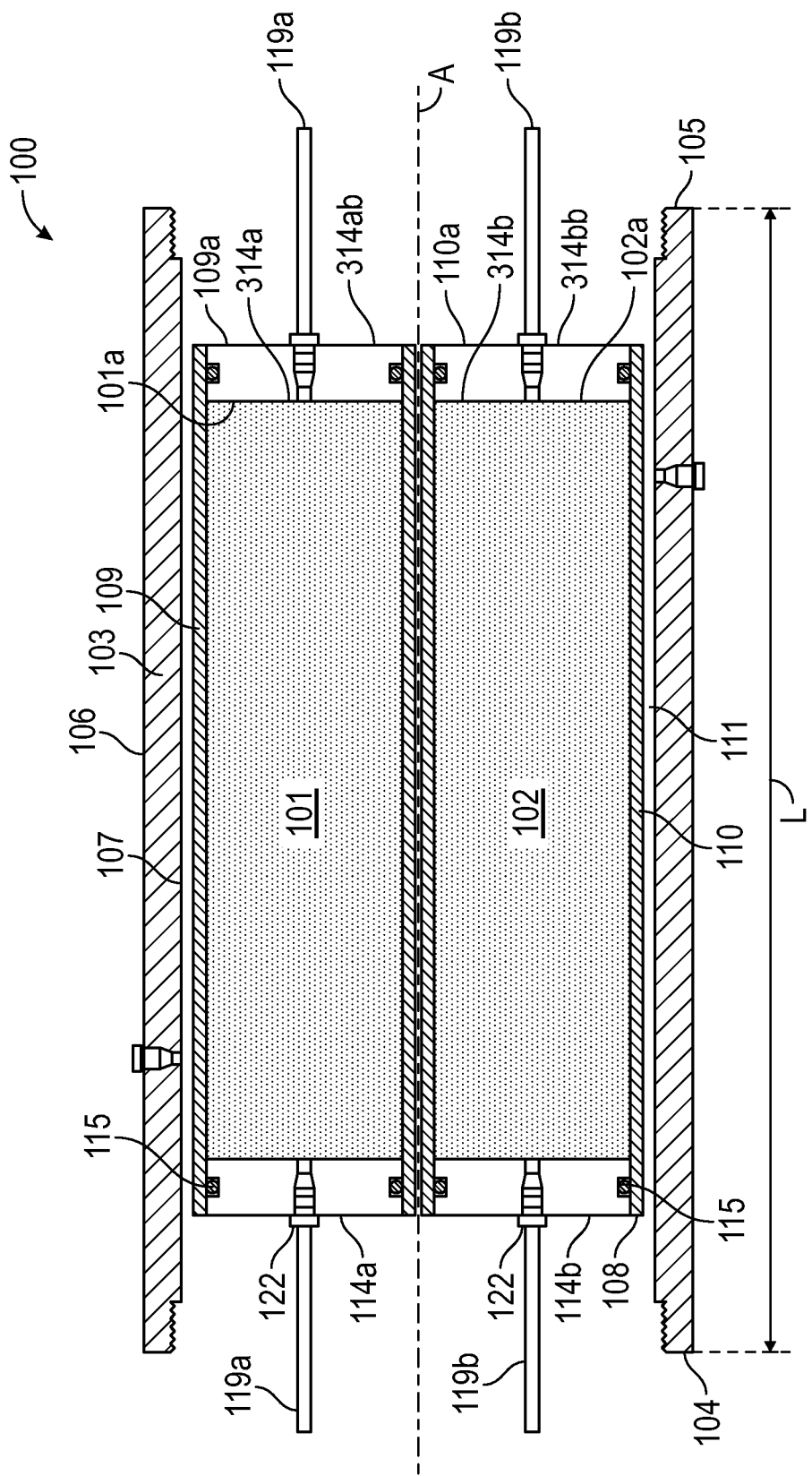

Now referring to FIG. 4, the first core and sleeve assembly and the second core and sleeve assembly are now loaded into the core sample holder 100. For example, the first core and sleeve assembly and the second core and sleeve assembly are inserted into the cavity 108 of the body 103. Additionally. the first core and sleeve assembly and the second core and sleeve assembly are positioned to be parallel with each other and offset from the axis A of the body 103. For example, the first core and sleeve assembly may be above the axis A and the second core and sleeve assembly may be below the axis A. Further, the first core and sleeve assembly and the second core and sleeve assembly are spaced a distance from the inner surface 107 of the body 103 to form the void space 111. The void space 111 may be a space within the cavity 108 not occupied by the first core and sleeve assembly and the second core and sleeve assembly.

In one or more embodiments, the length L of the body 103 is longer than the length of the first core and sleeve assembly and the second core and sleeve assembly. However, the first pair of tubes 119a and the second pair of tubes 119b extend out the first end surface 104 and the second end surface 105 of the body 103.

Figure 5A:
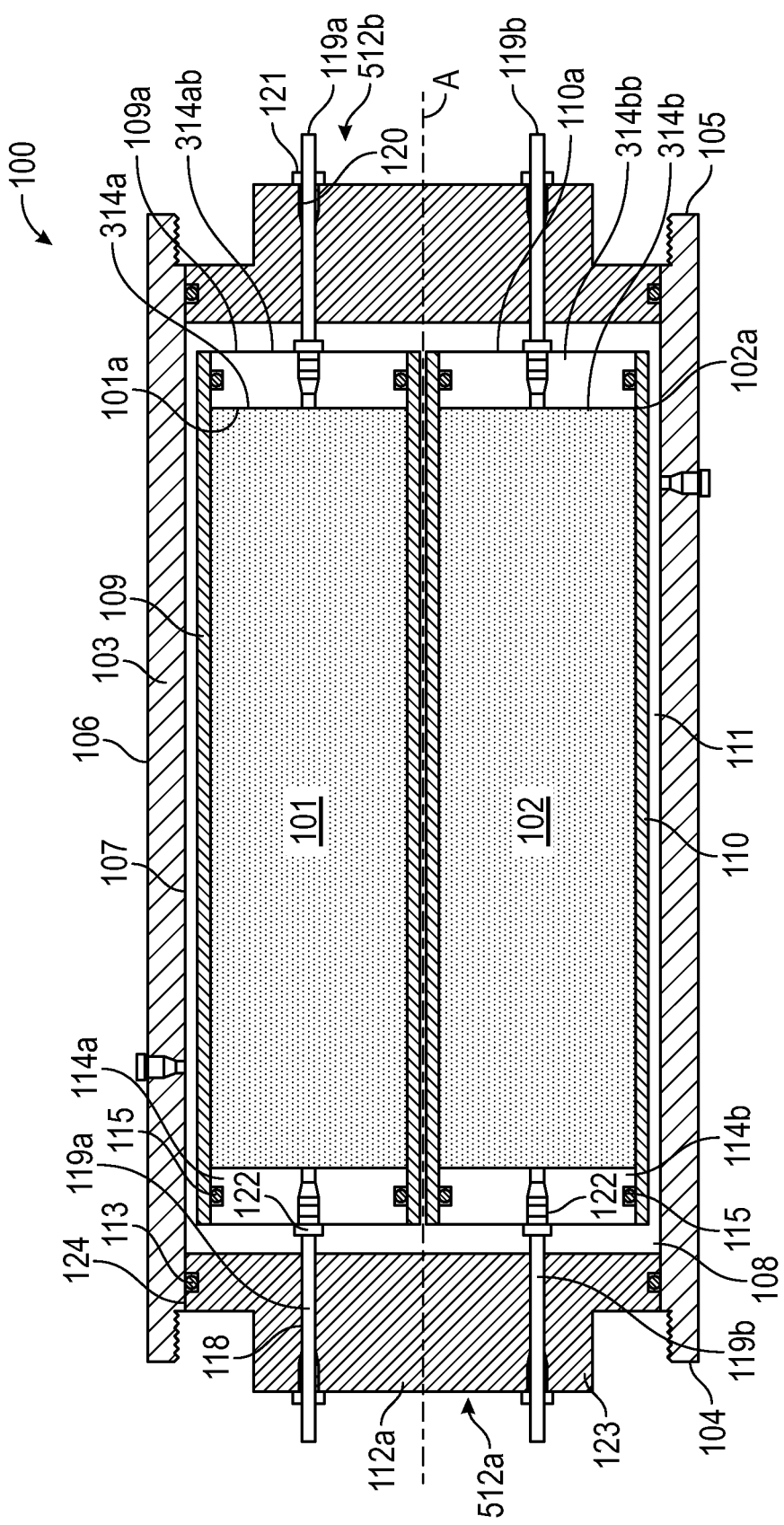
Figure 5B:
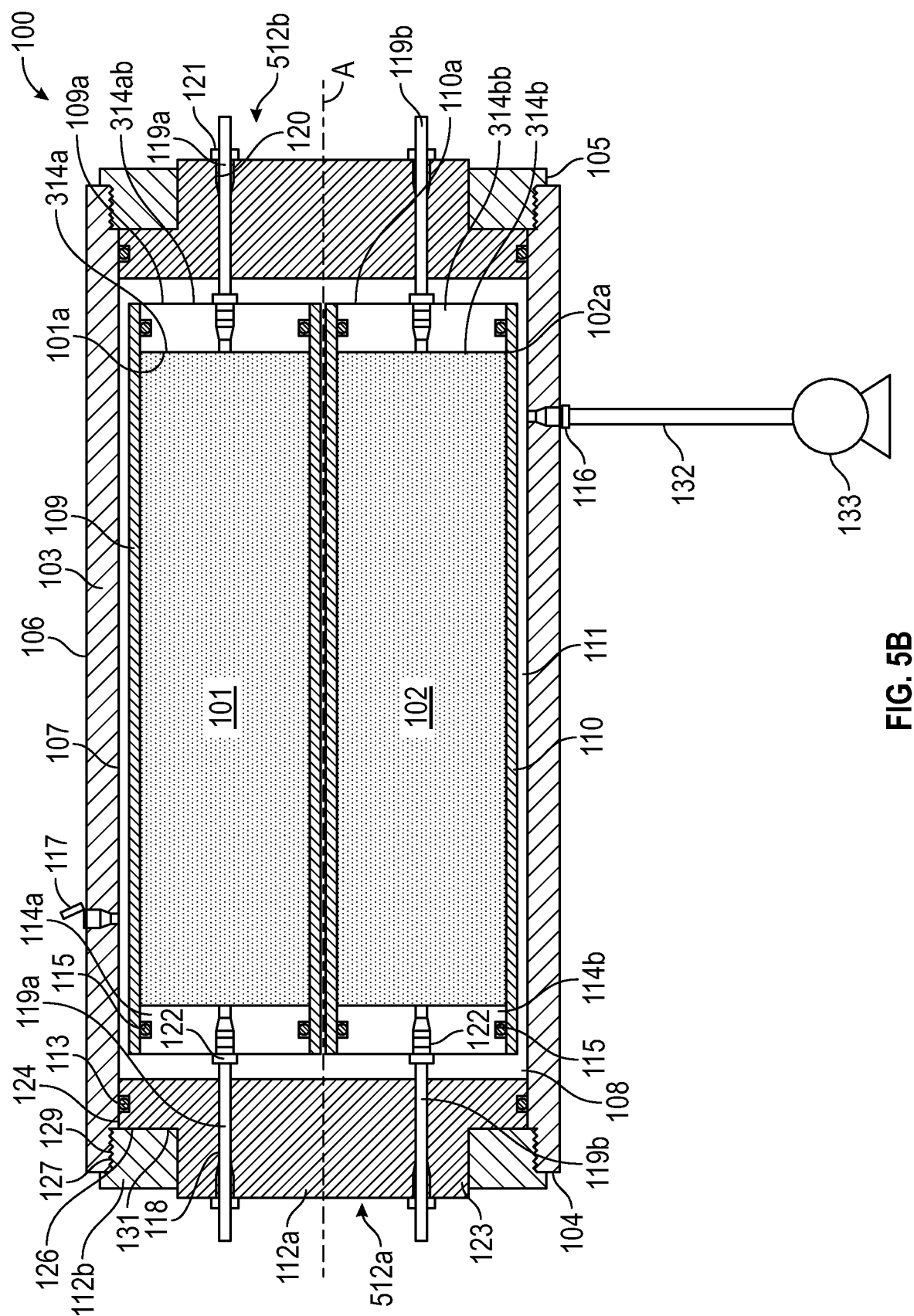

Referring now to FIGS. 5A and 5B, a first cap 512a and a second cap 512b are removably coupled to the body 103 to enclose the first core and sleeve assembly and the second core and sleeve assembly. The first cap 512a and the second cap 512b may be installed one after another or simultaneously. As shown in FIG. 5A, initially, the cap body 112a of each cap 512a, 512b is inserted into the openings of the body 103 such that the cap body 112a is within the cavity 108 of the body 103. From example, the sealing surface 124 of each cap 512a, 512b slides along the inner surface 107 of the body 103. The sealing element 113 on the sealing surface 124 seals against the inner surface 107. The flange 123 of each cap 512a, 512b extends out the body 103 past the corresponding end surface (104, 105). Additionally, the first pair of tubes 119a and the second pair of tubes 119b are slotted through the corresponding through holes 118 to protrude out of the flange 123. To seal the gap between each tube (119a, 119b) and each through hole 118, the O-ring 120 or elastomer seal is inserted between each tube (119a, 119b) and each through hole 118. Further, the nut 121 compressed the O-ring 120 within each cap 512a, 512b.

As shown in FIG. 5B, with the cap body 112a of each cap 512a, 512b positioned in the body 103, the cap retainer nut 112b of each cap 512a, 512b is removably coupled to the body 103 to retain the cap body 112a in place. For example, the passage of the cap retainer nut 112b is sled over the flange 123 such that the second end surface 126 of the cap retainer nut 112b contacts the load shoulder 131 of the cap body 112a. Additionally, the threads on the exterior surface 127 of the cap retainer nut 112b couples to the threads 129 on the inner surface 107 of the body 103 to lock/retain the cap body 112a within the body 103.

With each cap 512a, 512b removably coupled and locked to the body 103, a first flow line 132 is coupled to the first port 116. At an end distal to the first port 116, a pump 133 is coupled to the first flow line 132. The pump 133 pumps a fluid, such as hydraulic oil or water, through the first flow line 132 and fills the void space 111 in the cavity 108 via the first port 116. Additionally, the second port 117 is opened such that the air in the void space 111 is pushed out through the second port 117 as the void space 111 is being filled with the fluid. When the fluid is observed flowing out of second port 117 and gas bubbles have disappeared from the exiting fluid, the void space 111 is determined to be fully filled with the fluid.

Figure 6:
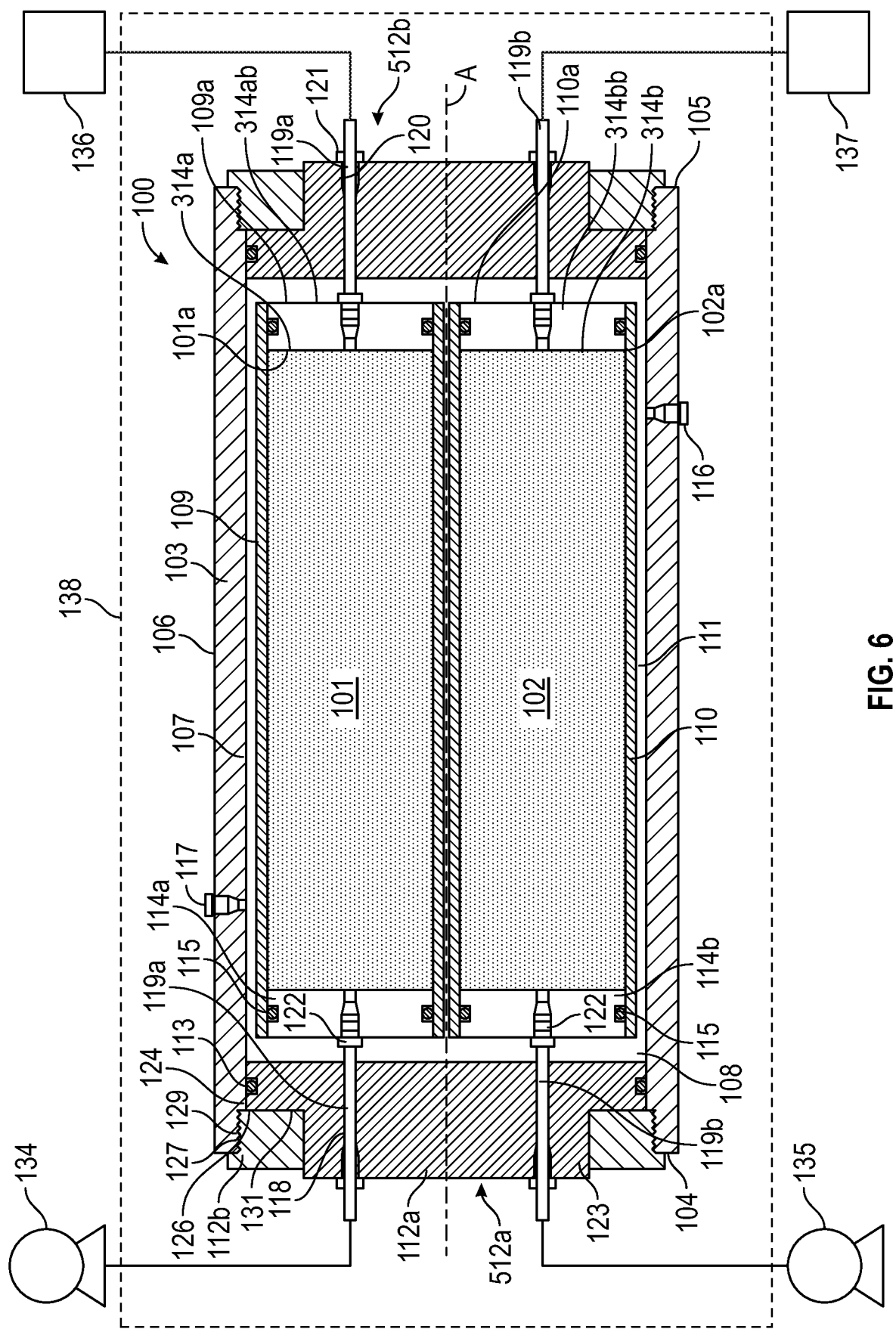

Now referring to FIG. 6, once the void space 111 is filled with the fluid, the second port 117 is closed to apply a target confining pressure on the first core sample 101 and the second core sample 102 in a radial direction. Additionally, the first flow line (132) may be removed from the first port 116 and the first port 116 is also closed to maintain the target confining pressure. Further, the first pair of tubes 119a and the second pair of tubes 119b may slightly move axially to apply a sample confining pressure on the first core sample 101 and the second core sample 102 in an axial direction.

In one or more embodiments, one or more pumps (134, 135) may be fluidly coupled to the first core sample 101 and the second core sample 102. For example, a discharge end of a first pump 134 is connected to a first tube of the first pair of tubes 119a at one end of the core sample holder 100. At the same end, a discharge end of a second pump 135 is connected to a first tube of the second pair of tubes 119b. In some embodiments, the same pump may be connected to both the first core sample 101 and the second core sample 102. Additionally, a second tube of the first pair of tubes 119a distal to the first tube of the first pair of tubes 119a is connected to a first drain tank 136. At the same end, a second tube of the second pair of tubes 119b distal to the first tube of the second pair of tubes 119b is connected to a second drain tank 137. It is further envisioned that a back pressure regulator (BPR) may be connected at each outlet before the drain tanks (136, 137). The BPR may be used to increase the fluid pressure inside the core samples (101, 102), which can simulate the actual reservoir fluid pressure.

In one or more embodiments, the core sample holder 100 may be mounted in an oven 138. The oven 138 controls a temperature at which core flooding tests may be conducted at. For example, the oven 138 may increase the temperature within the core sample holder 100 to be higher than a room temperature. The oven 138 may provide the core sample holder 100 with heat to replicate downhole temperatures. In some embodiments, a temperature sensor may be placed through additional ports (similar to ports 116, 117) extending through the wall of the body 103 to position the temperature sensor inside the core sample holder 100.

To use the setup in FIG. 6 for core flooding testing, fluids may be injected into the first core sample 101 and the second core sample 102 by the first pump 134 and the second pump 135, respectively. The fluid injection can be static or continuous over a predetermined measurement period. During this predetermined measurement period, the temperature may be adjusted by the oven 138. The injected fluids flow into the first core and sleeve assembly and the second core and sleeve assembly via dedicated inlet tubes (119a, 119b). The injected fluids travel through the first core sample 101 and the second core sample 102 and exit the first sleeve 109 and the second sleeve 110 via the dedicated outlet tubes (119a, 119b). From the dedicated outlet tubes, the injected fluids are deposited into the first drain tank 136 and the second drain tank 137. In some embodiments, the first drain tank 136 and the second drain tank 137 may be used to feed fluids back to the first pump 134 and the second pump 135.

In one or more embodiments, the fluids may be separately injected into each of the first core sample 101 and the second core sample 102. By separately injecting the fluids, multiple independent core flooding testing are conducted simultaneously using the same core sample holder at a same confining pressure and a same temperature. For example, a few different injecting fluids or different injection scenarios may be evaluated at a same time. Additionally, independent pressure and differential pressure measurements for each of the first core sample 101 and the second core sample 102 may be performed by connecting pressure sensors or transducers separately to the corresponding dedicated inlet and outlets.

In one or more embodiments, the same fluid may be injected simultaneously into both the first core sample 101 and the second core sample 102. By injecting the same fluid simultaneously, the core flooding tests are conducted as parallel flow in the first core sample 101 and the second core sample 102. This parallel flow may simulate a fluid flow in a multi-layer reservoir without crossflow. However, to simulate the parallel flow with partial crossflow, flow paths may be added along a length of the first core sample 101 and the second core sample 102 to connect the first core sample 101 and the second core sample 102 together.

After the predetermined measurement period, the first pump 134 and the second pump 135 may be disconnected. Once disconnected, the cavity 108 is bled via the second port 117 to remove pressure within the body 103. With pressure removed, the first cap 512a and a second cap 512b may be removed to recover the first core and sleeve assembly and the second core and sleeve assembly. Next, each of the plugs 114a, 114b are removed to access the first core sample 101 and the second core sample 102. The first core sample 101 and the second core sample 102 may then be analyzed to determine formation properties of the well such as porosity, permeability, fluid saturation, grain density and other characteristics to provide insight on the downhole conditions.

Figure 7:
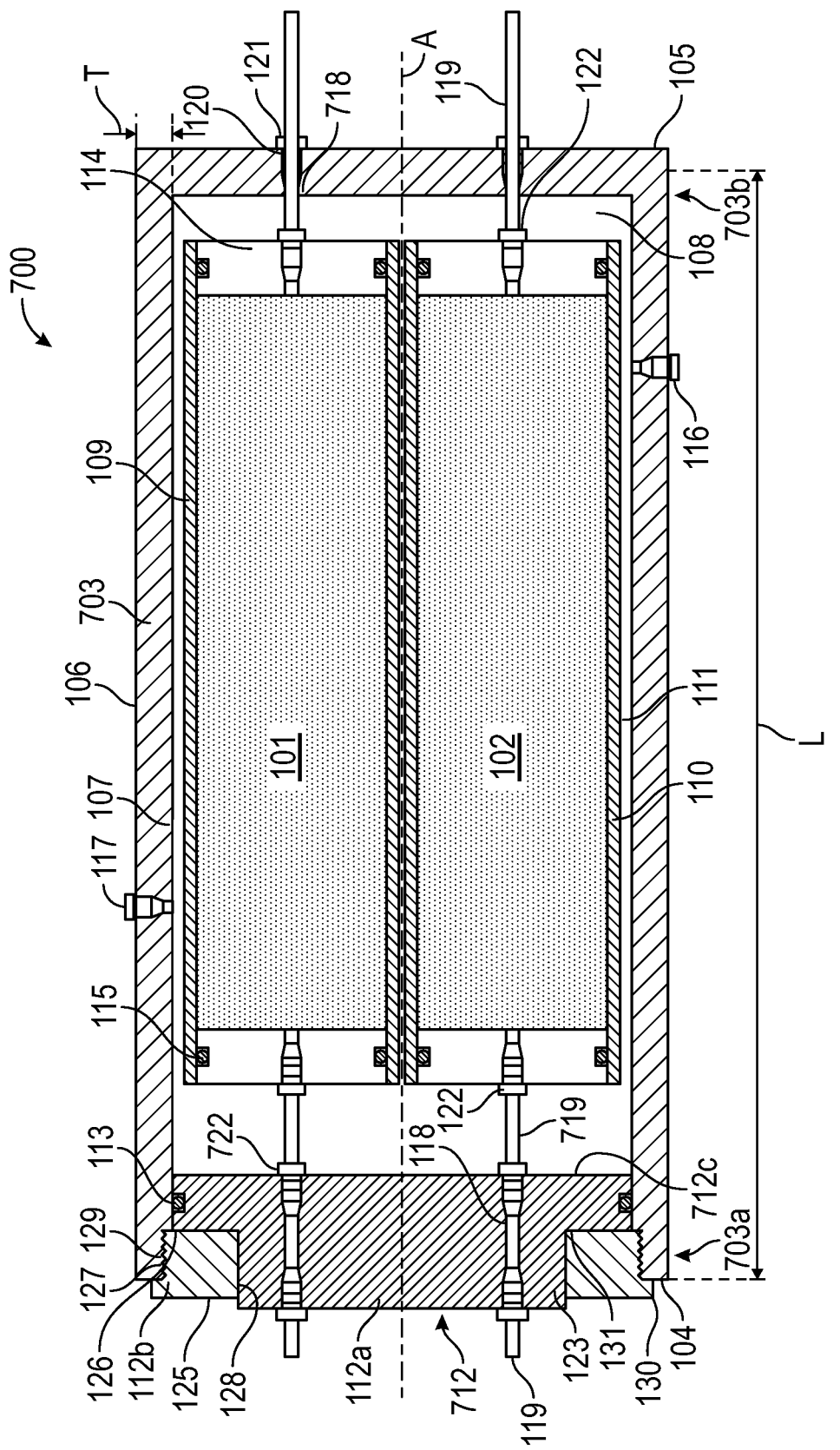
FIG. 7 illustrates a cross-sectional side view of a core sample holder in accordance with one or more embodiments of the present disclosure.

Referring now to FIG. 7, another embodiment of a core sample holder 700 according to embodiments herein is illustrated, where like numerals represent like parts. The embodiment of FIG. 7 is similar to that of the embodiment of FIG. 1. However, instead of having the body (103) with openings at both ends, the core sample holder 700 has a body 703 with an open end 703a and a closed end 703b.

In one or more embodiments, at the open end 703a of the body 703, an end cap 712 may be removably fixed within the body 703. The end cap 712 may be a fixed type end cap such that a distance between an end surface 712c of the end cap 712 and the core and sleeve assemblies are fixed. With the fixed end 712, a short-length tubing 719 fluidly connects the plugs 114 on the open end to the end cap 712 through the tubing fittings 722 in the end cap 712 and the tubing fittings 122 in the plugs 114. Additionally, the end cap 712 may also have the cap body 112a and the cap retainer nut 112b configurations as described in FIG. 1.

At the closed end 703b of the body 703, the wall of the body 703 may have holes 718 for each core and sleeve assembly. The holes 178 may have a diameter slightly larger than the outer diameter of tubes 119, which allow the tubes 119 to freely go through the wall and fluidly connect to the tubing fittings 122 of the corresponding plug 114.

In some embodiments, a combination of the core sample holder 100, 700 of FIGS. 1 and 7 may be used. For example, the fixed type end cap 712 may be used with one of the flexible or adjustable type end cap 112 in the body 103 of the core sample holder 100. Alternatively, the flexible or adjustable type end cap 112 may be used in the open end 703a of the body 703 distal to the closed end 703b.

Figure 8:
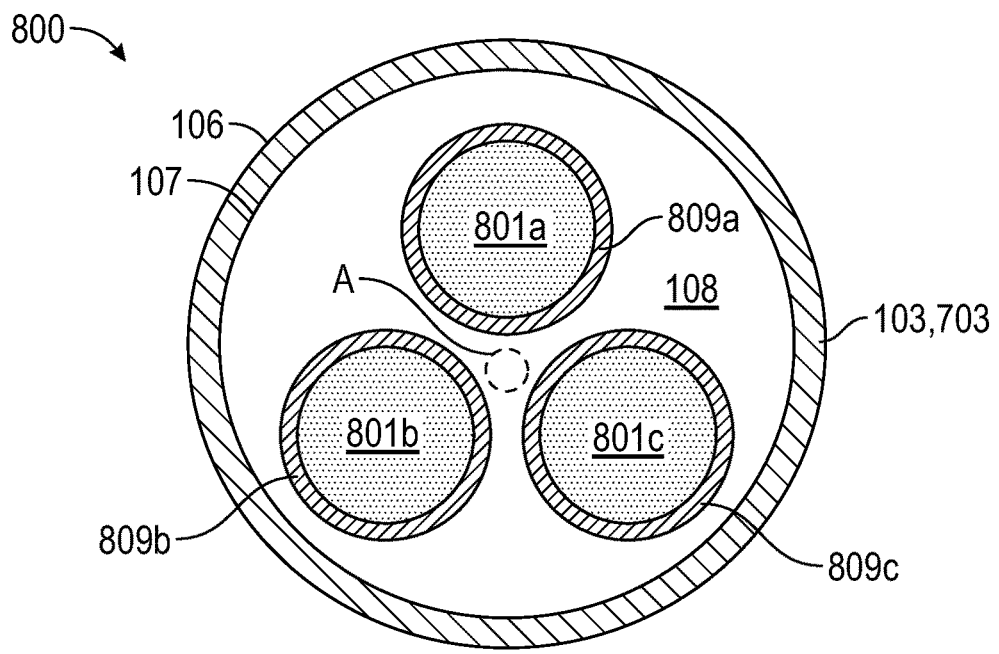
FIG. 8 illustrates a cross-sectional radial end view of a core sample holder in accordance with one or more embodiments of the present disclosure.

Referring now to FIG. 8, another embodiment of a core sample holder 800 according to embodiments herein is illustrated from a radial end view, where like numerals represent like parts. The embodiment of FIG. 8 is similar to that of the embodiment of FIGS. 1 and 7. For example, the core sample holder 800 may have either the body 103 or the body 703 from FIG. 1 or 7. However, instead holding two core samples, the core sample holder 800 holds at least three core samples 801a-801c each within individual sleeves 809a-809c. the at least three core samples 801a-801c are parallel to each other and evenly disturbed within the cavity 108. For example, each core samples 801a-801c may be disposed about the axis A every 120 degrees to be radially spaced within the cavity 108.

Figure 9:
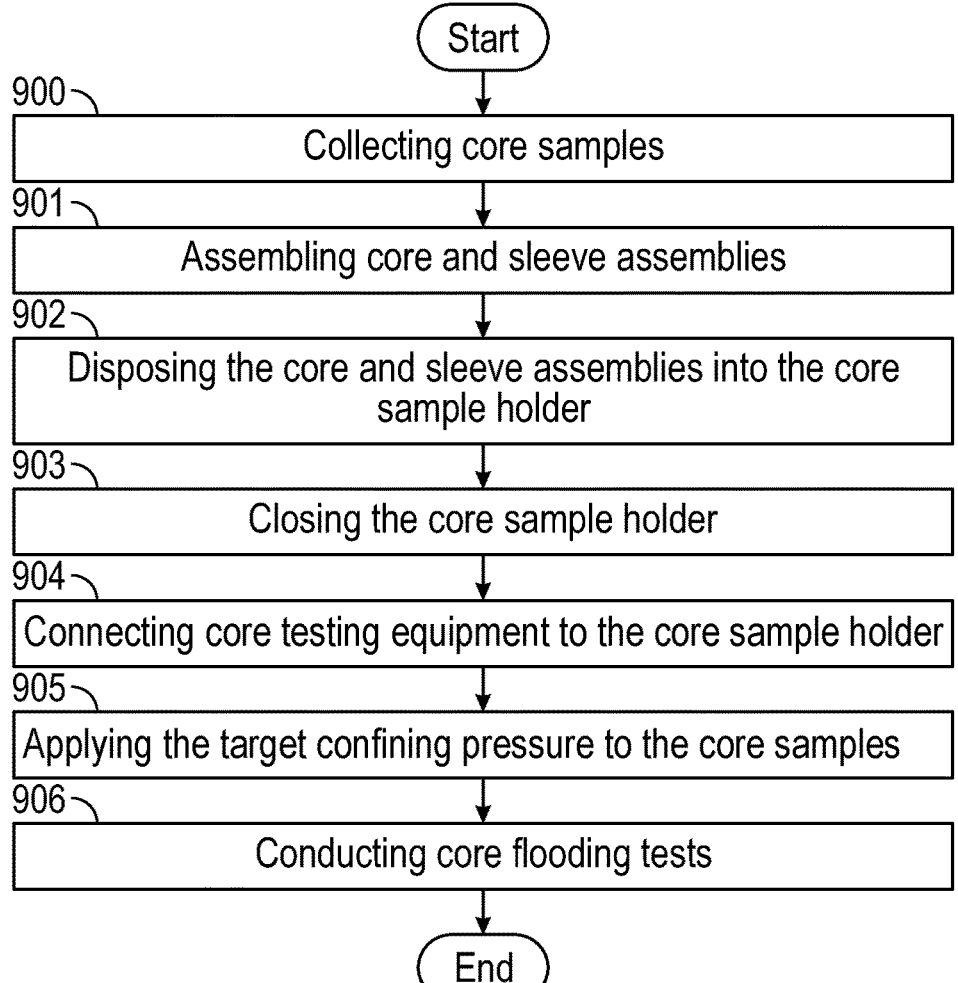
FIG. 9 illustrates flowchart for using a core sample holder in accordance with one or more embodiments of the present disclosure.

Referring to FIG. 9, in one or more embodiments, a flowchart for using the core sample holder (100, 700) as described in FIGS. 1-8 is illustrated for testing core samples. One or more steps in FIG. 9 may be performed by one or more components (for example, the computing system coupled to a controller in communication with core sample holder 100, 700) as described in FIGS. 1-8. For example, a non-transitory computer readable medium may store instructions on a memory coupled to a processor such that the instructions include functionality for operating various components on the core sample holder (100, 700).

In step 900, core samples are collected. For example, Initially, a formation of a well is drilled with a core drill bit. The core drill bit cuts core samples at various depths along the formation. The core samples are then transported to a surface for testing and data measurements. The core samples may be of various sizes and shapes.

In step 901, with the core samples collected, core and sleeve assemblies are assembled. For example, each core sample is individually inserted into corresponding sleeves. For example, one sleeve is dedicated for each core sample such that the number of sleeves corresponds to the number core samples. Once the core samples are within the sleeves, plugs are inserted into the ends of the sleeve to seal the core sample. For example, a first plug is inserted in a first opening of the sleeve and a second plug is inserted in a second opening of the sleeve distal to the first opening. The plugs contact the core samples to confine the core samples within the sleeve. Additionally, the O-ring of the plugs isolate the core samples such that the core samples may only be fluidly accessed by the tube fittings of the plugs. To finish assembly the core and sleeve assemblies, a tubing is inserted into each tubing fittings to fluidly access the core samples thereby forming the core and sleeve assemblies.

In step 902, each core and sleeve assembly are disposed in the core sample holder. For example, the core and sleeve assemblies are individually or together placed within the body of the core sample holder. The core and sleeve assemblies are evenly spaced within the cavity of the body to be parallel with each other. Additionally, the core and sleeves assemblies are offset from the axis of the body.

In step 903, the core sample holder is closed to isolate the core and sleeve assemblies within the cavity. For example, if the body of the core sample holder has two openings, a cap is inserted into each opening to fluidly isolate the core and sleeve assemblies. If the body of the core sample holder has only one opening, then a cap is inserted into the one opening to fluidly isolate the core and sleeve assemblies. Additionally, the caps have through holes such that the tubes extending from plug travel through the through holes to have an end of the tubes outside of the body.

In step 904, with the core sample holder closed, core testing equipment is connected to the core sample holder. For example, discharge ends of pumps are connected to first end of the core sample holder. Additionally, at an end distal to the first, drain tanks are coupled to the core sample holder. The target confining pressure is applied to the core samples. For example, a pump pumps fluids, such as hydraulic oil or water, into the first port to fill the void space in the cavity. Additionally, while the fluids are being pumped through the first port, air in the void spaces is pushed out of the second port. Once the void space is filled with the fluid, the second port is closed to apply the target confining pressure on the core samples in a radial direction. Further, the tubes move axially to apply a sample confining pressure on the core samples in an axial direction.

In step 905, with the core testing equipment connected to the core sample holder, the target confining pressure is applied to the core samples. For example, a pump pumps fluids, such as hydraulic oil or water, into the first port to fill the void space in the cavity. Additionally, while the fluids are being pumped through the first port, air in the void spaces is pushed out of the second port. Once the void space is filled with the fluid, the second port is closed to apply the target confining pressure on the core samples in a radial direction. Further, the tubes move axially to apply a sample confining pressure on the core samples in an axial direction.

In step 906, with the core testing equipment connected to the core sample holder, core flooding test are conducted. For example, fluids are pumped with the pumps through a dedicated inlet, enter the corresponding sleeve, pass over and through the core sample, and then exit the sleeve though a dedicated outlet. The dedicated inlet and the dedicated outlet may be at opposite ends of the sleeve. The dedicated inlet and the dedicated outlet may travel through the caps. It is further envisioned that the core sample holder may be placed in the oven to control a temperature at which the core flooding tests may be conducted at. For example, the oven may increase the temperature within the core sample holder to be higher than a room temperature.

In one or more embodiments, during the core flooding tests, the fluids may be separately injected into each second cores. By separately injecting the fluids, multiple independent core flooding testing are conducted simultaneously using the same core sample holder at a same confining pressure and a same temperature. For example, a few different injecting fluids or different injection scenarios may be evaluated at a same time. Additionally, independent pressure measurements for each core sample may be performed by connecting pressure transducers separately to the corresponding dedicated inlet and outlets. In some embodiments, the same fluid may be injected simultaneously into both the core samples. By injecting the same fluid simultaneously, the core flooding tests are conducted as parallel flow in the core samples. This parallel flow may simulate a fluid flow in a multi-layer reservoir without crossflow. However, to simulate the parallel flow with partial crossflow, flow paths may be added along a length of the core samples to connect the core samples together. After the core flooding test are completed, each of the core samples may then be analyzed to determine formation properties of the well such as porosity, permeability, fluid saturation, grain density and other characteristics to provide insight on the downhole conditions.

Figure 10:
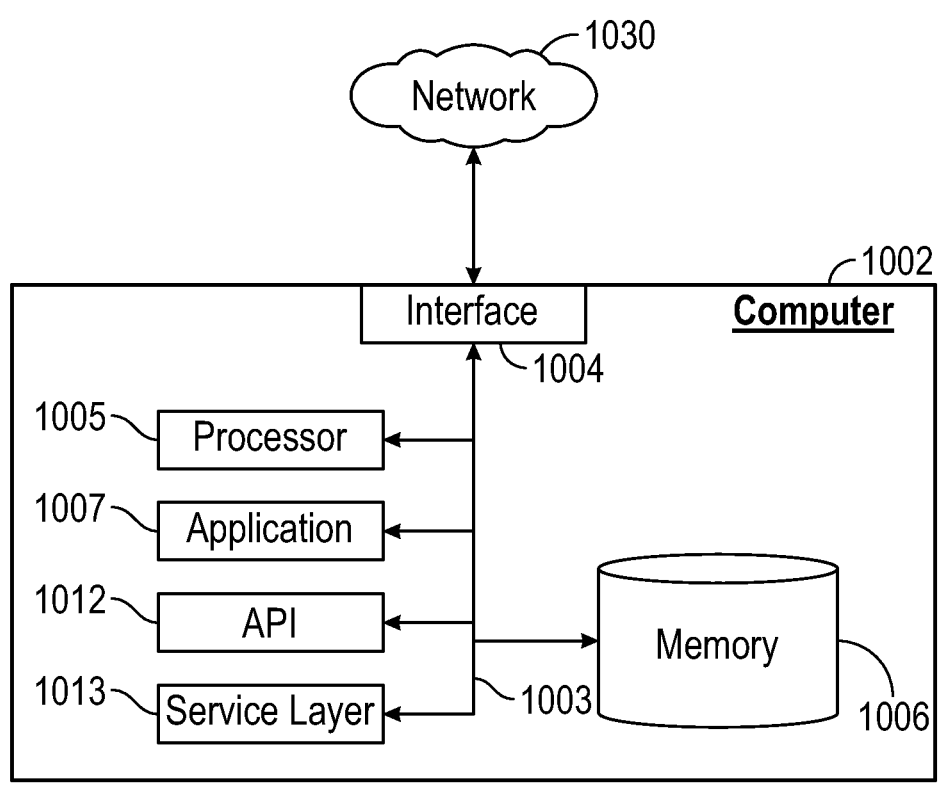
FIG. 10 illustrates a computer system in accordance with one or more embodiments of the present disclosure.

Embodiments disclosed herein for running a core flooding experiment using the core sample holder 100 may be implemented on a computing system. FIG. 10 is a block diagram of a computer system 1002 used to provide computational functionalities associated with described algorithms, methods, functions, processes, flows, and procedures as described in the instant disclosure, according to an implementation. The illustrated computer 1002 is intended to encompass any computing device such as a high-performance computing (HPC) device, a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer 1002 may include a computer that includes an input device, such as a keypad, keyboard, touch screen, or other device that can accept user information, and an output device that conveys information associated with the operation of the computer 1002, including digital data, visual, or audio information (or a combination of information), or a GUI.

The computer 1002 can serve in a role as a client, network component, a server, a database or other persistency, or any other component (or a combination of roles) of a computer system for performing the subject matter described in the instant disclosure. The illustrated computer 1002 is communicably coupled with a network 1030. In some implementations, one or more components of the computer 1002 may be configured to operate within environments, including cloud-computing-based, local, global, or other environment (or a combination of environments).

At a high level, the computer 1002 is an electronic computing device operable to receive, transmit, process, store, or manage data and information associated with the described subject matter. According to some implementations, the computer 1002 may also include or be communicably coupled with an application server, e-mail server, web server, caching server, streaming data server, business intelligence (BI) server, or other server (or a combination of servers).

The computer 1002 can receive requests over network 1030 from a client application (for example, executing on another computer 1002) and responding to the received requests by processing the said requests in an appropriate software application. In addition, requests may also be sent to the computer 1002 from internal users (for example, from a command console or by other appropriate access method), external or third-parties, other automated applications, as well as any other appropriate entities, individuals, systems, or computers.

Each of the components of the computer 1002 can communicate using a system bus 1003. In some implementations, any or all of the components of the computer 1002, both hardware or software (or a combination of hardware and software), may interface with each other or the interface 1004 (or a combination of both) over the system bus 1003 using an application programming interface (API) 1012 or a service layer 1013 (or a combination of the API 1012 and service layer 1013. The API 1012 may include specifications for routines, data structures, and object classes. The API 1012 may be either computer-language independent or dependent and refer to a complete interface, a single function, or even a set of APIs. The service layer 1013 provides software services to the computer 1002 or other components (whether or not illustrated) that are communicably coupled to the computer 1002. The functionality of the computer 1002 may be accessible for all service consumers using this service layer. Software services, such as those provided by the service layer 1013, provide reusable, defined business functionalities through a defined interface. For example, the interface may be software written in JAVA, C++, or other suitable language providing data in extensible markup language (XML) format or other suitable format. While illustrated as an integrated component of the computer 1002, alternative implementations may illustrate the API 1012 or the service layer 1013 as stand-alone components in relation to other components of the computer 1002 or other components (whether or not illustrated) that are communicably coupled to the computer 1002. Moreover, any or all parts of the API 1012 or the service layer 1013 may be implemented as child or sub-modules of another software module, enterprise application, or hardware module without departing from the scope of this disclosure.

The computer 1002 includes an interface 1004. Although illustrated as a single interface 1004 in FIG. 10, two or more interfaces 1004 may be used according to particular needs, desires, or particular implementations of the computer 1002. The interface 1004 is used by the computer 1002 for communicating with other systems in a distributed environment that are connected to the network 1030. Generally, the interface 1004 includes logic encoded in software or hardware (or a combination of software and hardware) and operable to communicate with the network 1030. More specifically, the interface 1004 may include software supporting one or more communication protocols associated with communications such that the network 1030 or interface's hardware is operable to communicate physical signals within and outside of the illustrated computer 1002.

The computer 1002 includes at least one computer processor 1005. Although illustrated as a single computer processor 1005 in FIG. 10, two or more processors may be used according to particular needs, desires, or particular implementations of the computer 1002. Generally, the computer processor 1005 executes instructions and manipulates data to perform the operations of the computer 1002 and any algorithms, methods, functions, processes, flows, and procedures as described in the instant disclosure.

The computer 1002 also includes a memory 1006 that holds data for the computer 1002 or other components (or a combination of both) that can be connected to the network 1030. For example, the memory 1006 can be a database storing data consistent with this disclosure. Although illustrated as a single memory 1006 in FIG. 10, two or more memories may be used according to particular needs, desires, or particular implementations of the computer 1002 and the described functionality. While the memory 1006 is illustrated as an integral component of the computer 1002, in alternative implementations, memory 806 can be external to the computer 1002.

The application 1007 is an algorithmic software engine providing functionality according to particular needs, desires, or particular implementations of the computer 1002, particularly with respect to functionality described in this disclosure. For example, the application 1007 can serve as one or more components, modules, applications, etc. Further, although illustrated as a single application 1007, the application 1007 may be implemented as multiple applications 1007 on the computer 1002. In addition, although illustrated as integral to the computer 1002, in alternative implementations, the application 1007 can be external to the computer 1002.

There may be any number of computers 1002 associated with, or external to, a computer system containing computer 1002, each computer 1002 communicating over the network 1030. Further, the term "client," "user," and other appropriate terminology may be used interchangeably as appropriate without departing from the scope of this disclosure. Moreover, this disclosure contemplates that many users may use one computer 1002, or that one user may use multiple computers 1002.

In some embodiments, the computer 1002 is implemented as part of a cloud computing system. For example, a cloud computing system may include one or more remote servers along with various other cloud components, such as cloud storage units and edge servers. In particular, a cloud computing system may perform one or more computing operations without direct active management by a user device or local computer system. As such, a cloud computing system may have different functions distributed over multiple locations from a central server, which may be performed using one or more Internet connections. More specifically, cloud computing system may operate according to one or more service models, such as infrastructure as a service (IaaS), platform as a service (PaaS), software as a service (Saas), mobile "backend" as a service (MBaaS), serverless computing, artificial intelligence (AI) as a service (AIaaS), and/or function as a service (FaaS).

In addition to the benefits described above, the systems and methods of the present disclosure may be used to log and map out the saturation, pressure, and temperature profiles of the multiple core samples either in static or dynamic (continuous injection) modes at the same time. Overall, the core sample holder may minimize product engineering, risk associated with core flooding experiments, reduction of assembly time, hardware cost reduction, and weight and envelope reduction.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, any means-plus-function clauses are intended to cover the structures described herein as performing the recited function(s) and equivalents of those structures. Similarly, any step-plus-function clauses are intended to cover the acts described here as performing the recited function(s) and equivalents of those acts. It is the express intention of the applicant not to invoke 35 U.S.C. § 112(f) for any limitations of any of the claims herein, except for those in which the claim expressly uses the words "means for" or "step for" together with an associated function.

What is claimed is:

1. A core sample holder for testing core samples from a well, the core sample holder comprising:
   a body having a wall defining a cavity;
   at least two sleeves disposed within the cavity parallel to each other, wherein each sleeve of the at least two sleeves is configured to individually hold the core samples;
   at least one cap removably coupled to an inner surface of the wall; and
   a tube extending from each end of the at least two sleeves to be a dedicated inlet at a first end of each sleeve and a dedicated outlet at a second end of each sleeve, wherein each tube is configured to individually hold a fluid.

2. The core sample holder of claim 1, wherein the at least two sleeves are spaced a distance inward from the inner surface of the wall.

3. The core sample holder of claim 1, further comprising plugs inserted at the first end of each sleeve and the second end of each sleeve.

4. The core sample holder of claim 3, further comprising a tubing fitting in each plug to fluidly couple each tube to the at least two sleeves.

5. The core sample holder of claim 3, further comprising a seal provided between the plugs and the at least two sleeves.

6. The core sample holder of claim 1, further comprising a seal provided between the at least one cap and the inner surface.

7. The core sample holder of claim 1, wherein each of the tubes extend through holes of the at least one cap.

8. The core sample holder of claim 1, wherein the at least two sleeves are made from a rubber material or a heat-shrinkable material.

9. The core sample holder of claim 1, wherein the body comprises a first port to fill a void space between the at least two sleeves and the wall with fluids.

10. The core sample holder of claim 9, wherein the body comprises a second port to release air from the void space.

11. The core testing system of claim 1, wherein at least one fluid is held by the tube extending from one of the at least two sleeves and at least one different fluid is held by the tube extending from another of the at least two sleeves.

12. A core testing system for testing core samples from a well, the core testing system comprising:
- a core sample holder having a body to hold at least two core and sleeve assemblies parallel to each other within a cavity of the body, wherein each of the at least two core and sleeve assemblies comprises:
  - a sleeve;
  - a core sample inserted in the sleeve;
  - a first plug closing a first end of the sleeve and a second plug closing a second end of the sleeve to isolate the core sample; and
  - a pair of tubes fluidly coupled to a tubing fitting in the first plug and the second plug to form a dedicated inlet at the first plug and a dedicated outlet at the second plug; and
- at least two pumps, wherein each pump is fluidly coupled to at least one dedicated inlet extending out of the body of the core sample holder, and wherein the at least two pumps are configured to individually inject fluids into each of the at least two core and sleeve assemblies.

13. The core testing system of claim 12, further comprising at least one drain tank fluidly coupled to the dedicated outlet to receive fluids exiting each of the at least two core and sleeve assemblies.

14. The core testing system of claim 12, wherein the core sample holder is mounted in an oven.

15. The core testing system of claim 12, wherein at least one fluid is injected through one of the at least two core and sleeve assemblies and at least one different fluid is injected through another of the at least two core and sleeve assemblies.

16. A method for testing core sample from a well, the method comprising:
- collecting at least two core samples;
- placing each core sample of the at least two core samples individually within a corresponding sleeve to form at least two core and sleeve assemblies in parallel;
- disposing the at least two core and sleeve assemblies within a cavity of a core sample holder;
- applying a target confining pressure to the at least two core samples; and
- injecting fluids through the at least two core samples,
- wherein at least one fluid is injected through one of the at least two core samples and at least one different fluid is injected through another of the at least two core samples.

17. The method of claim 16, further comprising sealing each core sample of the at least two core samples with plugs inserted at ends of the corresponding sleeve.

18. The method of claim 17, further comprising inserting tubes into the plugs to form a dedicated inlet at one end of the corresponding sleeve and a dedicated outlet at an opposite end of the corresponding sleeve.

19. The method of claim 18, wherein injecting fluids through the at least two core samples comprise flowing the fluids via a pump through the dedicated inlet into the sleeve, flowing the fluids over and through the at least two core samples, and exiting the fluids out of the corresponding sleeve via the dedicated outlet.

20. The method of claim 16, wherein applying the target confining pressure comprises pumping fluids via a first port into the cavity and pushing air out of the cavity via a second port.

* * * * *